United States Patent [19]
Swierczek et al.

[11] Patent Number: 5,402,798
[45] Date of Patent: Apr. 4, 1995

[54] DISPOSABLE SKIN PERFORATOR AND BLOOD TESTING DEVICE

[76] Inventors: Remi Swierczek, 720 Madison Ave., Painesville, Ohio 44077; Anatol Topolewski, 21603 Greenwood Dr., Kildear, Ill. 60047

[21] Appl. No.: 45,893

[22] Filed: Apr. 12, 1993

Related U.S. Application Data

[63] Continuation-in-part of Ser. No. 732,109, Jul. 18, 1991, Pat. No. 5,201,324.

[51] Int. Cl.$^6$ ............................................ A61B 5/00
[52] U.S. Cl. ................................. 128/770; 606/182
[58] Field of Search .................. 128/770, 760, 763; 606/181, 182, 185

[56] References Cited

U.S. PATENT DOCUMENTS

| | | | |
|---|---|---|---|
| 4,469,110 | 9/1984 | Slama | 128/770 |
| 4,715,374 | 12/1987 | Maggio | 606/182 |
| 4,817,603 | 4/1989 | Turner et al. | 606/182 |
| 4,869,249 | 9/1989 | Crossman et al. | 606/182 |
| 4,892,097 | 1/1990 | Ranalletta et al. | 606/182 |
| 4,990,154 | 2/1991 | Brown et al. | 606/182 |
| 5,026,388 | 6/1991 | Ingalz | 606/182 |
| 5,054,499 | 10/1991 | Swierczek | 128/770 |
| 5,100,427 | 3/1992 | Crossman et al. | 606/182 |
| 5,201,324 | 4/1993 | Swierczek | 128/770 |
| 5,231,993 | 8/1993 | Haber et al. | 128/770 |
| 5,269,799 | 12/1993 | Daniel | 606/182 |

FOREIGN PATENT DOCUMENTS 3515420 10/1986 Germany ............................ 128/770

*Primary Examiner*—Stephen C. Pellegrino
*Assistant Examiner*—Guy V. Tucker
*Attorney, Agent, or Firm*—Oldham, Oldham & Wilson Co.

[57] ABSTRACT

A device (20) that pierces the skin due to the collapsing of dome (1) between the fingertips. Immediately after a puncture is made, a blood or exudate sample can be collected. A shutter device (50) is incorporated into the skin perforator to prevent repeated use of the device.

13 Claims, 5 Drawing Sheets

DISPOSABLE SKIN PERFORATOR AND BLOOD TESTING DEVICE

This is a continuation in part application of Ser. No. 07/732,109, filed on Jul. 19, 1991, now U.S. Pat. No. 5,201,324.

TECHNICAL FIELD

This invention, generally, relates to a device for drawing a small amount of blood from a person's fingertip. More specifically, the invention relates to a single use device for obtaining a blood sample and employing a means for preventing multiple use of the device.

BACKGROUND OF THE INVENTION

Blood testing is a common practice. Blood samples can be obtained by merely pricking the fingertip with a sharp tool. The samples are subsequently exposed to proper test medium to acquire a test result. In the past, a variety of complex, sudden release, pen type devices with disposable needles were used to perforate the skin. However, due to the complexity and ominous appearance of these devices patient compliance and acceptance has been less than desirable. Therefore, due to the deficiencies of the prior art, applicants invention is herein presented.

SUMMARY OF THE INVENTION

In accordance with the embodiments of the present invention, this device is a disposable skin perforator for obtaining a sample of blood by puncturing the skin further employing a mechanism for ensuring the one time use of the device.

Therefore, one objective of the present invention is to provide a simple, painless and inexpensive fingertip perforator that draws a sample of blood for testing and self-analysis.

A further object of the present invention is to provide a skin perforator for obtaining a blood sample which employs a means for preventing multiple use of the same device. Other objectives of my invention will become clear with reference to the accompanying figures.

DETAILED DESCRIPTION OF THE PREFERRED EMBODIMENT

Figure 1:
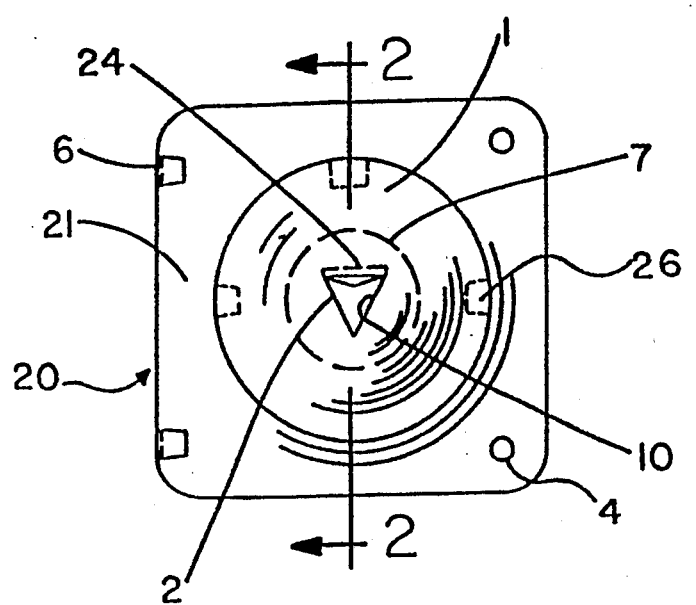
FIG. 1 is a plan view of the perforator device.

Now with reference to the invention illustrated in the drawings, and looking particularly at FIG. 1, this figure shows a top plan view of the perforator device 20. Perforator device 20 comprises generally a cover plate 21 and a pressure plate 3 of essentially similar size and shape positioned adjacent to one another and attached by a plurality of welds 4 and/or crimps 6.

Cover plate 21 has a spherical shaped dome 1 formed therein so as to define a convex surface with respect to said cover plate 21 and directed outward and away from said pressure plate 3. Cover plate 21 with spherical dome 1 formed integrally therein is made of a resilient plastic or thin metal material having a substantial memory so that as dome 1 is deflected inward by a force it will return to essentially its original shape upon the removal of said force.

Pressure plate 3 is to have a rigid structure as compared to dome 1 and may be made from any plastic or metal material capable of maintaining such rigidity. Welds 4 or crimps 6 of varying number and size are contemplated. Pressure plate 3 has an aperture 7 formed generally in the center of said pressure plate 3 and having sufficient diameter to allow the passage of a barb 2 through the aperture 7. Shelf 23 defines the periphery of said aperture 7.

A barb 2 is formed in a portion of dome 1 utilizing stamping methods which are well known in the art. Barb 2 remains integral with dome 1 along edge 24 of barb 2. Barb 2 is disclosed as being essentially triangular in shape however, any shape which yields a point capable of piercing the human skin is contemplated. The stamping of dome 1 to form barb 2 results in an aperture having essentially the same dimensions as said barb 2. Barb 2 is formed so as to be directed inward and toward the aperture 7 of plate 3. After stamping, barb 2 can be coined or shaved to yield sharp yet smooth edges, by any means which are well known in the art. Alternatively, such edges of barb 2 can be achieved by grinding the same, but grinding currently appears not to be a cost effective method as related to this application.

Dome 1 serves as a stress accumulating means wherein said dome 1 offers increasing resistance to applied pressure, directed inward, until said dome is deformed to an extent that it begins to undergo an inversion. At this point, resistance to the applied pressure decreases rapidly such that the central region of dome 1 containing the barb is accelerated inward and toward aperture 7 of pressure plate 3. With continued pressure dome 1 is inverted, directing barb 2 through aperture 7 and into the adjacent skin, thereby creating a puncture site.

An alternative embodiment is contemplated wherein said cover plate 21 and said pressure plate 3 are made from a single piece of material. Cover plate 21 and pressure plate 3 are folded against each other so as to share a common edge, the outer edges of each plate being secured to one another utilizing welds 4 or crimps 6 as discussed previously herein.

In its inverted state, dome 1 assumes an essentially cantilever configuration which accumulates a force opposing the inversion and aids in the resilient return of dome 1 to its convex configuration.

Figure 3:
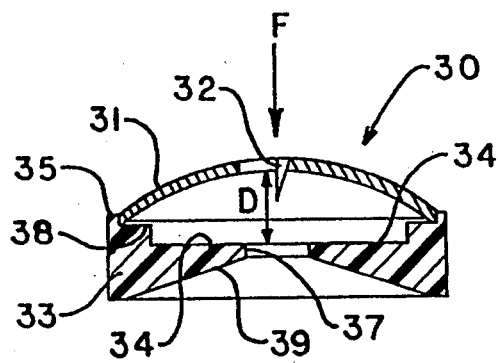
FIG. 3 is a cross-sectional view of an alternative embodiment of a skin perforator according to the present illustrating a dome in its uncollapsed position.
Figure 4:
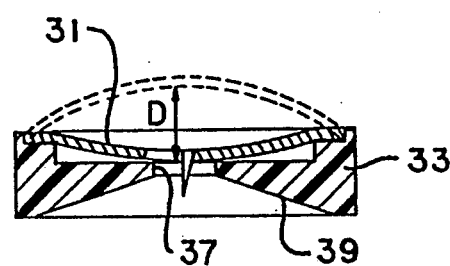
FIG. 4 is a cross-sectional view of the skin perforator shown in FIG. 3 and illustrating the dome in its collapsed position.

FIGS. 3 and 4 disclose an alternative embodiment 30 of the skin perforator. The pressure plate 33 is preferably made from a molded plastic material and is essentially annular in shape. A convex dome 31, similar to dome 1 of FIG. 1 and having a point penetrating barb 32, is seated on a step 38 and inside of an outer rim 35 in pressure plate 33. Pressure plate 33 contains an aperture 37 in its center which allows passage of barb 32 therethrough. Shelf 34 serves to stop the inversion of dome 31, thereby controlling the depth of barb 32 into the patient's skin.

In order to achieve a quick and relatively painless penetration of the skin, distance D between the peak of dome 31, in its undepressed state, and shelf 34 of pressure plate 33 is preferably at least about 0.10 inches. While this distance is not absolute, it has been calculated to account for a minimum stroke depth, deflection waste and differences in patient skin texture. According to the present embodiments, the minimum depth stroke is identified as that minimum distance necessary for the dome to undergo its inversion and is estimated at 0.050 inches. The deflection waste refers to the movement of the dome 31 toward the puncture site upon the application of force but prior to the dome's inversion and is calculated at about 0.025 inches. Approximately 0.030 inches is necessary to account for differences in the thickness and texture of the skin at the puncture site. A distance D ranging from about 0.075 inches to about 1.025 inches insures penetration of the skin coupled with a positive return of the inverted dome to its convex configuration.

The embodiment 20 or 30 of the present invention are designed to perforate the skin on the finger of the patient. The finger should be prepared so as to cleanse and remove as many contaminates from the perforation site as is possible using techniques which are well known in the art.

Figure 5:
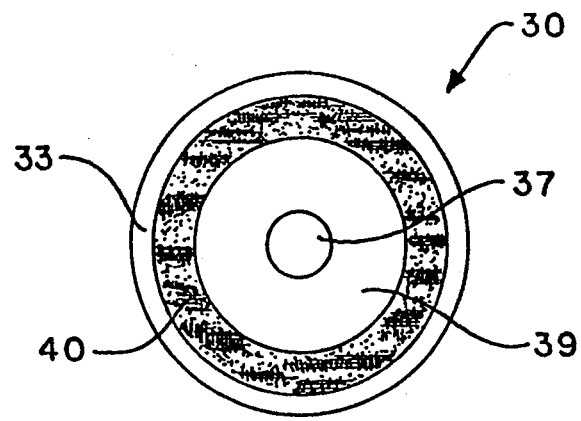
FIG. 5 is a bottom elevational view of an alternative embodiment of a skin perforator according to the present invention illustrating a self contained means for cleansing and/or disinfecting the puncture site.

Optionally, any of the embodiments disclosed herein are contemplated as capable of incorporating a self-contained cleaning means disclosed in FIG. 5. Device 30 is shown as incorporating an absorbent pad, impregnated with a cleansing and/or disinfecting agent, affixed to the lower surface 39 of pressure plate 33, adjacent the patient's skin.

The absorbent pad 40 is intended to be made from any cotton, synthetic or other fiber commonly used in the art for such purpose and capable of retaining liquid therein. The cleansing or disinfecting agents can be selected from any such agents known in the art, including but certainly not limited to ethyl alcohol, isopropyl alcohol or benzalkonium chloride. The eventual puncture site can then be cleansed or disinfected by rubbing lower surface 39 of device 30 over the site. Often times, the puncture site is a fingertip, at which time the device is simply rubbed between the thumb and fingertip. In this manner, the eventual puncture site is cleansed and prepared to receive the point penetrating barb. Alternatively, pad 40 could be nonimpregnated or impregnated with a testing reagent and absorb blood from the puncture site for analysis.

Figure 2:
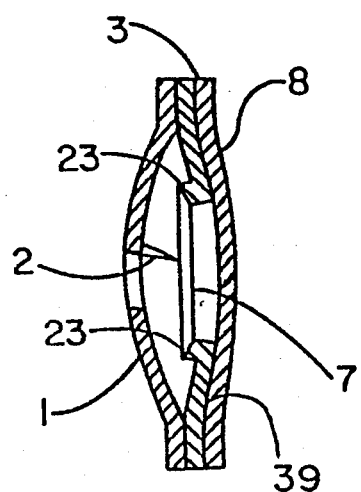
FIG. 2 is a cross-sectional view taken on line 2—2 of FIG. 1.

The lower surface 39 of pressure plates 3 or 33 are may be aseptically covered or sealed to keep the surface free from contaminates and to prevent evaporation of the cleansing agent. Immediately prior to use, a packaging seal such as is shown by reference number 8 in FIG. 2, is removed thus exposing the device and/or lower surface 39.

Figure 6:
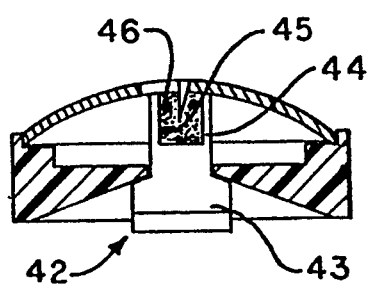
FIG. 6 is a cross-sectional view of a skin perforator according to the present invention and illustrating a removable guard incorporated therein for maintaining the sterility of the barb until use.

FIG. 6 reveals an alternative means for preserving the sterility of barb 32 until just prior to the time of desired use. This packing means is disclosed as a tab 42 having a base portion 43 and a stem 44. The stem 44 is formed with a cavity 45 open at the end opposite base 43. Cavity 45 has a depth at least equal to the length of barb 32 in dome 31. Cavity 45 is capable of receiving a wax or other medium exhibiting properties of a solid at or above room temperature but liquefying in the presence of heat. Additionally, such medium must possess the ability to prevent or resist the growth of bacteria, fungi and other microbes, either inherently or by the addition of antimicrobials.

Following the sterilization of barb 32 after assembly, cavity 45 in stem 44 is filled with a medium 46 in a liquid or semi-solid state. Immediately thereafter, barb 32 is inserted into the medium contained in cavity 45. Thereupon cooling, a frangible connection between tab 42 and barb 32 is formed. Tab 42 is removed prior to use of the skin perforator by pliably moving tab 42 relative to device 30. Other means of frangibly connecting tab 42 about barb 32 as are known in the art to accomplish the same or similar purpose, are contemplated, such as ultrasonic welding and the like.

Turning again to FIGS. 1–2 but having applicability to all embodiments, the device 20 operated by positioning device 20 against the patient's finger to be punctured so that the intended puncture site of the finger comes within an area defined by the outer circumference of aperture 7 in pressure plate 3. Pressure is then applied to the dome by the patient or person assisting the same. The initial applied pressure causes pressure plate 3 to be pressed against the skin of the patient further isolating the intended puncture site. As additional pressure is applied to dome 1 the stress accumulation in the dome will result in the sudden inward collapsing of dome 1, directing barb 2 through aperture 7, thereby causing a piercing of the patient's skin. This inward movement of barb 2 is stopped as the inner surface of dome 1 strikes shelf 23 of pressure plate 3 to provide a predictable puncture depth.

As the applied pressure on dome 1 and pressure plate 3 is removed or reduced, the collapsed dome will resiliently return to its original shape and accordingly withdraw barb 2 from the patient's finger. The maintenance of a small amount of pressure against pressure plate 3, but pressure insufficient to cause collapse of dome 1, will create a tension to the area around the puncture site, resulting in an enhanced and continuous blood flow from the puncture site. This applied tension has a twofold effect with respect to enhanced blood flow. First, this tension maintains the skin in a stretched posture which holds edges of the puncture site apart. Second, the pressure applied to the region surrounding the puncture site forces blood out of this tissue and into adjacent tissue which may be outside or inside of this ring of applied pressure. The blood directed inward seeks relief from this pressure and as a result exits through the puncture site. How enhancement of the blood from the puncture site is also increased by the creation of a partial vacuum or pressure differential within the confined area defined by dome 1, pressure plate 3 and the patient's finger. This area as defined while the dome is in the collapsed position, has a comparatively reduced volume compared to the same area with dome 1 in its original position. While in the depressed position, the person administrating the applied force may simply cover or obstruct aperture 10 formed from the stamping of barb 2, as the pressure is withdrawn. This sudden increase in volume in the area enclosed by the pressure plate 3 and dome 1 creates a vacuum at the aperture 7. The vacuum causing free flow of blood from the puncture site.

After the barb has been withdrawn from the finger, the disposable skin perforator can be removed and a blood sample collected as in prior art devices by squeezing the finger, if necessary.

The skin perforators of the present invention are intended as disposable or single use devices, unless the devices are resterilized after each use by means known in the art. In this way, the risk of patient contamination resulting from the use of unsterile or tainted devices is minimized. In furtherance of this objective, the skin perforator shown in copending application Ser. No. 07/732,109 illustrates various shutter means for preventing repeated use of the device. A further preferred embodiment of the present invention, employing a shutter means herein in FIGS. 7-12.

Generally, the device is fully functional upon its removal from the aseptic packaging. The device is used to perforate the skin of a patent for the purposes of obtaining a blood sample by placing the pressure plate in contact with the skin and applying force to the convex dome as previously described. In these embodiments, the force applied to cause inversion of the dome resulting in the puncture of dome by barb 32 is also utilized to activate a shutter means 50, previously loaded in its tensioned position. Upon retraction of the dome, the shutter means so will advance to its untensioned position between barb 32 and aperture 37. In this way, subsequent attempts to utilize device 30 as a skin perforator will force barb 32 against a shutter shield 52, preventing puncture of the patient's skin. Once the shutter means 50 has advanced to its untensioned position between barb 32 and aperture 37, the device is disabled and to be discarded.

Figure 7:
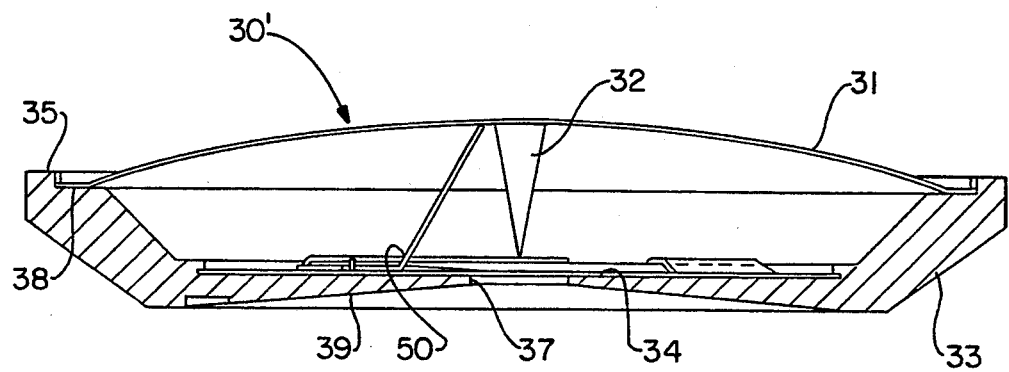
FIG. 7 is a cross-sectional view of a preferred embodiment of the present invention employing a shutter means.
Figure 8:
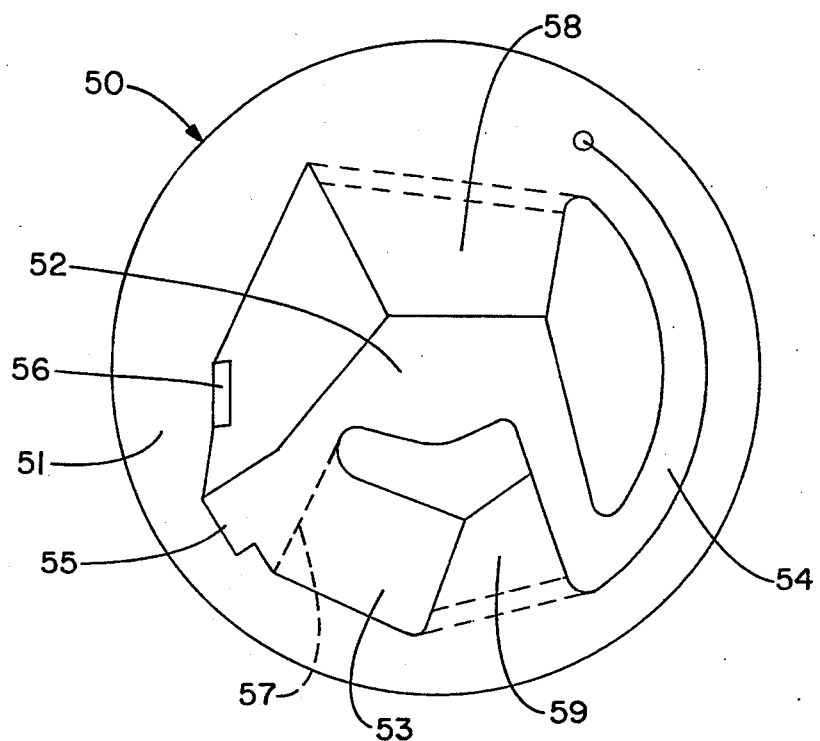
FIG. 8 is a bottom elevational view of the preferred embodiment illustrating the shutter means of the present invention in its untensioned state.

Specifically, FIGS. 7-12 illustrate one embodiment of a shutter means 50 for preventing repeated use of a skin perforator. FIG. 8 discloses shutter means, generally 50, comprising a thin shutter disc 51, having a shield member 52 and a spring portion 54 most preferably formed by a stamping process. The spring portion 54 is contemplated as an arc-shaped ribbon of spring like material having a substantially long term memory so as to return to its original untensioned position even after extended periods of time in a tensioned state. Such suitable materials include but are not limited to various types of plastics or aluminum. The proximal end of spring portion 54 is shown as attached to the body of shutter disc 51.

With continued reference to FIG. 8, a shield member 52 is secured to the distal end of spring 54. The shield member 52 is preferably intended as having a total area approximately equal or greater to aperture 37 and in its untensioned position is located directly above aperture 37. Actuating member 53 and retaining member 55 are integral with and located at the opposite end of shield member 52 from spring portion 54.

Stop member 56 is located interior of the periphery of shutter disc 51 and on the side opposite said spring member 54. Stop member 56 extends upward toward said dome 31 and serves to maintain the shutter means 50 in a tensioned position until completion of the device's initial use.

During assembly and packaging, actuating member 53 is folded upward toward said dome along line 57 as best shown in FIG. 8. Guide surfaces 58 and 59 are folded along the lines on their respective surfaces as again shown in FIG. 8. Guide surface 58 functions to limit the angular deflection of shield 52 while guide surface 59 controls the angular deflection of said spring 54.

Figure 9:
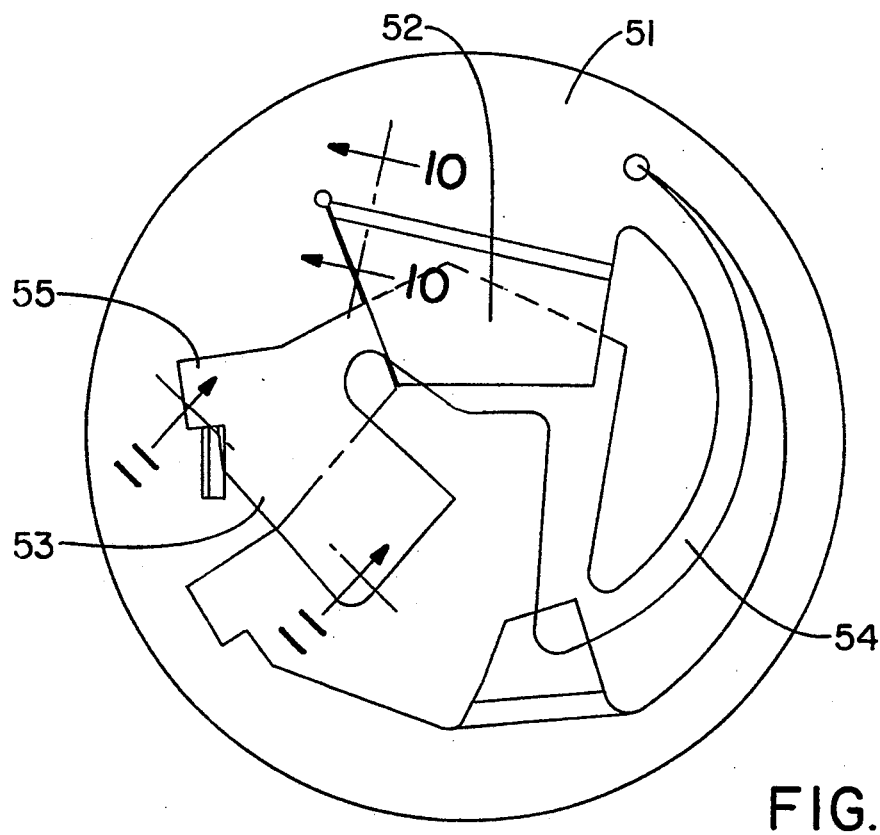
FIG. 9 is a bottom elevational view of the embodiment of the present invention of FIGS. 7-8 and illustrating the shutter means in its tensioned position.
Figure 10:
FIG. 10 is a cross-sectional view of a portion of the shutter means as taken through lines 10—10 of FIG. 9.
Figure 11:
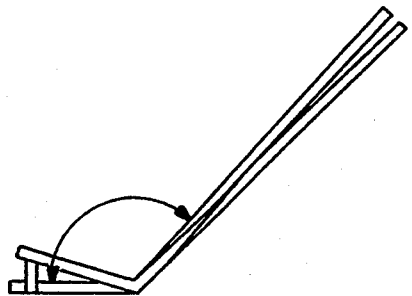
FIG. 11 is a cross sectional view a portion of the shutter means as taken through lines 11—11 of FIG. 9.

As shown in FIG. 7, during assembly of skin perforator 30, the preformed and folded shutter means 50 is placed on the lower shelf 34 of pressure plate 33. Subsequently the shutter assembly comprising the shield 52, actuating member 53 and retaining member 55 connected to spring member 54 is rotationally pivoted so as to tension spring portion 54 and hold said assembly in a tensioned state by placing said retaining member 55 behind said stop member 56, as shown in FIGS. 7, 9 and 11. In the tensioned position, actuating member 53 is angled upward toward said dome 31.

Figure 12:
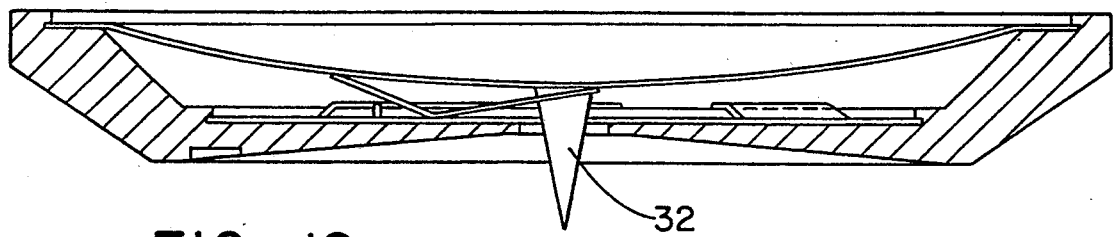
FIG. 12 is a cross-sectional view of the preferred embodiment of the present invention disclosed in FIG. 7 and illustrating the dome in its collapsed position.

As illustrated in FIG. 12, upon compression of dome 31 from applied force, the actuating member 53 is deflected downward as the barb penetrates the skin effectively lifting retaining member 55 over said stop member 56. Upon retraction of dome 31 to its original position, shutter means 50 advances to its untensioned position as illustrated in FIG. 8 with shield 52 covering aperture 37. In this way, subsequent attempts to utilize device 30 will result in the barb's contact with shield 52 thereby preventing additional punctures of the skin using the same device.

The shutter means 50 as illustrated in the embodiments previously disclosed herein need only possess sufficient tension to enable it to position itself between the barb and the aperture. Preferably the tension applied to the shutter means is not so great as to cause contact with the barb, while in the patient's skin.

The shutter means detailed in the drawings and specification of this application are illustrative and not to be construed as limited to the specific embodiments set forth herein. It is contemplated that the self-contained cleansing means and the shutter means have application well beyond the scope of the specific embodiments of skin perforators disclosed in this application.

Hence the foregoing embodiments are designed to be simple in construction, economical to manufacture and capable of being packaged under sterile conditions. While in accordance with the patent statutes the best mode and preferred embodiment of the invention have been described, it is to be understood that the invention is not limited thereto, but is rather to be measured by the scope and the spirit of the appended claims.

What is claimed is:

1. A skin perforator for puncturing the skin, said perforator of the type comprising a housing having a contact surface for placement adjacent to the skin to be punctured, an aperture in said contact surface, a puncturing member operatively mounted within said housing for movement towards and through said aperture, upon the application of applied force said puncturing member penetrating into the skin, wherein the improvement comprises:

a shutter means for automatically occluding the aperture of said skin perforator from movement of said puncturing member therethrough following initial puncture of the skin, wherein said shutter means is formed from a unitary disk positioned between said puncturing member and said contact surface in said housing.

2. The skin perforator as recited in claim 1 wherein said shutter means comprises a shield portion and a spring portion, said spring portion capable of accepting applied tension and having a memory so as to predictably advance said shield portion over said aperture in said contact surface upon removal of said tension.

3. The skin perforator as recited in claim 1 wherein said shutter means further comprises a stop member for retaining said shutter means in a tensioned position.

4. The skin perforator as recited in claim 1 further comprising a pad attached to said contact surface to absorb blood or exudate flowing from a puncture site formed by the penetration of said barb.

5. The skin perforator as recited in claim 4 wherein said pad is treated with at least one reagent for medical analysis.

6. The skin perforator as recited in claim 4 wherein said pad is impregnated with a skin preparatory agent comprising one or more from the group consisting of ethyl alcohol, isopropyl alcohol, benzalkonium chloride, iodine, and topical antimicrobials.

7. The skin perforator as recited in claim 1 wherein said shutter means is activated by the initial puncture of the skin.

8. The skin perforator as recited in claim 7 wherein said activation is initiated by the application of said applied force.

9. A skin perforator for obtaining a sample of, blood by puncturing the skin comprising:

a) a pressure plate containing an aperture formed therein wherein said pressure plate is adapted to be placed adjacent to the area of skin to be punctured;

b) a cover plate having a resilient convex panel formed therein, said cover plate being attached to said pressure plate and said convex panel having a point penetrating barb and directed inward toward said aperture in said pressure plate wherein a pressure applied to the convex panel and directed toward said pressure plate overcomes the resistance of said convex panel and said convex panel undergoes at least a partial inversion to cause said barb to suddenly and rapidly penetrate the skin causing a puncture, said convex panel having a memory so as to resiliently return to its original convex shape upon removal of said pressure thereby withdrawing the barb from the skin, and c) a shutter means capable of automatically occluding the aperture of said pressure plate from movement of said puncturing member therethrough following the initial penetration wherein said shutter means is formed from a unitary disk positioned between said puncturing member and said contact surface in said housing.

10. The skin perforator as recited in claim 1 wherein said shutter means comprises a shield portion and a spring portion, said spring portion capable of accepting applied tension and having a memory so as to predictably advance said shield portion over said aperture in said contact surface upon removal of said tension.

11. The skin perforator as recited in claim 9 wherein said skin perforator further comprises a stop member for retaining said shutter in a tensioned position.

12. The skin perforator as recited in claim 9 wherein said shutter means is activated by the initial puncture of the skin.

13. The skin perforator as recited in claim 12 wherein said activation is initiated by the application of said applied force.

* * * * *